(12) United States Patent
Teague et al.

(10) Patent No.: US 7,803,176 B2
(45) Date of Patent: Sep. 28, 2010

(54) STERNAL CLOSURE CLAMP DEVICE

(75) Inventors: Michael Teague, Jacksonville, FL (US); Shawn Burke, Jacksonville, FL (US)

(73) Assignee: KLS-Martin, L.P., Jacksonville, FL (US)

( * ) Notice: Subject to any disclaimer, the term of this patent is extended or adjusted under 35 U.S.C. 154(b) by 472 days.

(21) Appl. No.: 11/506,677

(22) Filed: Aug. 18, 2006

(65) Prior Publication Data
US 2007/0043371 A1 Feb. 22, 2007

Related U.S. Application Data

(60) Provisional application No. 60/709,532, filed on Aug. 19, 2005.

(51) Int. Cl.
*A61B 17/04* (2006.01)
*A61B 1/32* (2006.01)
*A44B 1/04* (2006.01)

(52) U.S. Cl. .................. 606/300; 600/215; 600/218; 600/219; 24/309; 24/329; 24/376

(58) Field of Classification Search ........... 600/215, 600/210, 218, 219, 225; 606/60, 213, 216, 606/250–3, 256–8, 264, 276, 280, 905, 218, 606/220; 24/309, 327, 329, 376; 623/17.12
See application file for complete search history.

(56) References Cited

U.S. PATENT DOCUMENTS

| 583,455 | A |  | 6/1897 | Bush |  |
|---|---|---|---|---|---|
| 1,969,188 | A | * | 8/1934 | Spicer | 606/216 |
| 3,473,528 | A |  | 10/1969 | Mishkin et al. |  |
| 4,199,182 | A | * | 4/1980 | Sunesson | 24/68 CD |
| 4,201,215 | A |  | 5/1980 | Crossett et al. |  |
| 4,279,248 | A |  | 7/1981 | Gabbay |  |
| 4,583,541 | A |  | 4/1986 | Barry |  |
| 5,139,498 | A |  | 8/1992 | Astudillo |  |
| 5,246,443 | A | * | 9/1993 | Mai | 606/78 |
| 5,440,790 | A | * | 8/1995 | Chou | 24/302 |
| 5,608,951 | A | * | 3/1997 | Chou | 24/302 |
| 5,759,193 | A | * | 6/1998 | Burbank et al. | 606/213 |
| 5,941,881 | A |  | 8/1999 | Barnes |  |
| 6,051,007 | A |  | 4/2000 | Hogendijk et al. |  |
| 6,287,308 | B1 | * | 9/2001 | Betz et al. | 606/263 |
| 6,302,899 | B1 |  | 10/2001 | Johnson et al. |  |
| 6,540,769 | B1 |  | 4/2003 | Miller, III |  |
| 6,603,051 | B1 | * | 8/2003 | Beaudry | 602/41 |

(Continued)

FOREIGN PATENT DOCUMENTS

EP 246086 A2 * 11/1987

*Primary Examiner*—Thomas C Barrett
*Assistant Examiner*—David W Bates
(74) *Attorney, Agent, or Firm*—Thomas C. Saitta (57) ABSTRACT

A sternal closure clamp device for securing and retaining longitudinally divided halves of a sternum, the device having four laterally extending engagement members that are positioned in inter-rib spaces on both sides of the sternum. The engagement members are connected to a centralized main body in a manner that allows the engagement members to be shortened or contracted such that the sternal halves may be pressed together and held in abutting relation. Each of the engagement members contracts in a direction non-perpendicular to the sternal incision, and the engagement members on a given side are non-parallel to each other such that device has a generally X-shaped configuration.

16 Claims, 7 Drawing Sheets

U.S. PATENT DOCUMENTS

| | | |
|---|---|---|
| 6,712,821 B2 | 3/2004 | Gabbay |
| 6,872,210 B2 | 3/2005 | Hearn |
| 7,033,377 B2 * | 4/2006 | Miller, III .................... 606/213 |
| 2004/0093024 A1 * | 5/2004 | Lousararian et al. ......... 606/213 |
| 2007/0049967 A1 * | 3/2007 | Sibbitt et al. ................. 606/213 |
| 2007/0203399 A1 * | 8/2007 | Gephart et al. .............. 600/219 |

* cited by examiner

STERNAL CLOSURE CLAMP DEVICE

This application claims the benefit of U.S. Provisional Patent Application Ser. No. 60/709,532, filed Aug. 19, 2005.

BACKGROUND OF THE INVENTION

This invention generally relates to devices used to rejoin a human sternum that has been severed longitudinally, and more particularly relates to such devices that function in a clamping manner to retain the severed sternum portions in a closed and abutting relationship post-operatively.

It is often necessary in surgical operations to longitudinally sever the patient's sternum so that the ribs may be spread to provide access to internal organs such as the heart. It is then necessary to secure the sternum halves together for post-operative recovery. Various closure techniques are used to accomplish this task. For example, holes may be drilled into the sternum halves and suture material passed through and tightened to cinch the sternum halves together. Apertured plates may be added to further rigidify the sternum post-operatively, with the suture material being passed through the apertures in the plate and the sternum. Encircling members may be wrapped around the sternum and tightened. Toothed bridging members extending across the cut line may be pressed into the sternum surfaces and/or secured with threaded rods extending between the sternal halves.

Another sternal closure technique involves the use of clamps having hook-like projections or engagement members on both ends, the clamp being positioned laterally relative to the sternal incision with the projections being disposed between adjoining rib pairs. The clamp is then linearly contracted or compressed to shorten the device and force the sternal halves together, the clamp typically comprising two members joined in a linear telescoping manner. Locking or securing means, either permanent or releasable, maintain the clamp in the contracted configuration.

Examples of such techniques and devices are described in U.S. Pat. No. 3,473,528 to Mishkin et al., U.S. Pat. No. 4,201,215 to Crossett et al., U.S. Pat. No. 4,279,248 to Gabbay, U.S. Pat. No. 4,583,541 to Barry, U.S. Pat. No. 5,139,498 to Astudillo Ley, U.S. Pat. No. 6,051,007 to Hogendijk et al., U.S. Pat. No. 6,217,580 to Levin, U.S. Pat. No. 6,302,899 to Johnson et al., U.S. Pat. No. 6,540,769 to Miller, III, and U.S. Pat. No. 6,712,821 to Gabbay.

It is an object of this invention to provide a sternal closure clamp device having the functionality of a contractible sternal clamp, such that the sternal halves may be quickly and easily pressed or drawn together in a sliding or telescoping manner and retained in position, but which provides greater reinforcement and rigidity to the severed sternum. It is a further object to provide such a sternal closure clamp device where the stress applied against the sides of the sternal halves is more widely dispersed than with conventional clamps. It is a further object to provide such a sternal closure clamp device whereby a single device is secured in two inter-rib spaces on each side of the sternum rather than in just one inter-rib space on each side. It is a further object to provide such a sternal closure clamp having four engagement members that are each disposed between different rib pairs, wherein the engagement members contract and extend in a direction non-perpendicular to the sternal incision, such that the clamp device is generally X-shaped. It is a further object to provide an embodiment of a sternal closure clamp device wherein the engagement members are pivotable such that the relative angles of the engagement members can be varied. It is a further object to provide an embodiment of a sternal closure clamp device wherein the engagement members are extendible and contractible independently. It is a further object to provide an embodiment of a sternal closure clamp device wherein the engagement members are extendible and contractible in unison utilizing a single control mechanism.

SUMMARY OF THE INVENTION

The invention is in general a sternal closure clamp device for post-operatively closing, securing and supporting a patient's sternum that has been longitudinally severed into two sternal halves. The sternal clamp generally comprises a centralized body member and four laterally-extending engagement members that extend from the body member, with two engagement members extending to one side and two engagement members extending to the other side. The engagement members are means to engage, secure or otherwise retain the sternal halves in an abutting relationship, with the engagement members having hooks, projections, fingers or the like extending in the posterior direction, whereby the engagement members can be disposed against the outer edges of the sternal halves and between adjoining ribs, preferably with the two engagement members located on a given side being positioned in the inter-rib spaces to either side of a single rib. The engagement members are adjustable relative to the main body, such that the overall length of the engagement members or the distance between the engagement members and the main body can be shortened to press or draw the sternal halves together. The engagement members extend in directions non-perpendicular to the sternal incision line, such that the device has a generally X-shaped configuration and functionality. The sternal clamp further comprises locking means to secure and retain the engagement members in the contracted position, with the locking means preferably being releasable. Most preferably, the engagement members may be both shortened and extended relative to the main body. In certain embodiments, a contracting means, such as a centralized knob, may be provided whereby simultaneous contraction of the four engagement members can be accomplished by operation of the contraction means. The engagement members may be contracted independently in certain embodiments and simultaneously in other embodiments. In certain embodiments, the engagement members are pivotable relative to the main body, such that the contraction direction and the angle between the engagement members can be varied.

DETAILED DESCRIPTION OF THE INVENTION

With reference to the drawings, the invention will now be described in detail with regard for the best mode and the preferred embodiment. The invention is a sternal closure clamp device used to close, secure and support a sternum post-operatively, the sternum having been severed longitudinally into left and right lateral sternal halves to provide access to the interior of the chest.

Broadly the invention may be defined as a sternal closure clamp device comprising a central body; four engagement members, two of said engagement members mounted on a first side of said central body and the other two of said engagement members mounted on a second side of said central body, wherein said two engagement members on said first side of said central body are positioned non-parallel to each other and said two engagement members on said second side of said central body are positioned non-parallel to each other; wherein said engagement members are retractable toward said central body. Alternatively, the invention may be broadly defined as a sternal closure clamp device securing a sternum longitudinally divided into first and second sternal halves in abutting relationship, said device comprising a central body; four engagement members slidingly received by said central body in a manner whereby said engagement members can be retracted toward said central body, said engagement members comprising arm members and projection members extending generally perpendicularly from said arm members, two of said engagement members mounted on a first side of said central body and the other two of said engagement members mounted on a second side of said central body, wherein said two engagement members on said first side of said central body are positioned non-parallel to each other and with said projection members disposed on opposite sides of a rib of said first sternal half, and wherein said two engagement members on said second side of said central body are positioned non-parallel to each other and with said projection members disposed on opposite sides of a rib of said second sternal half.

Figure 1:
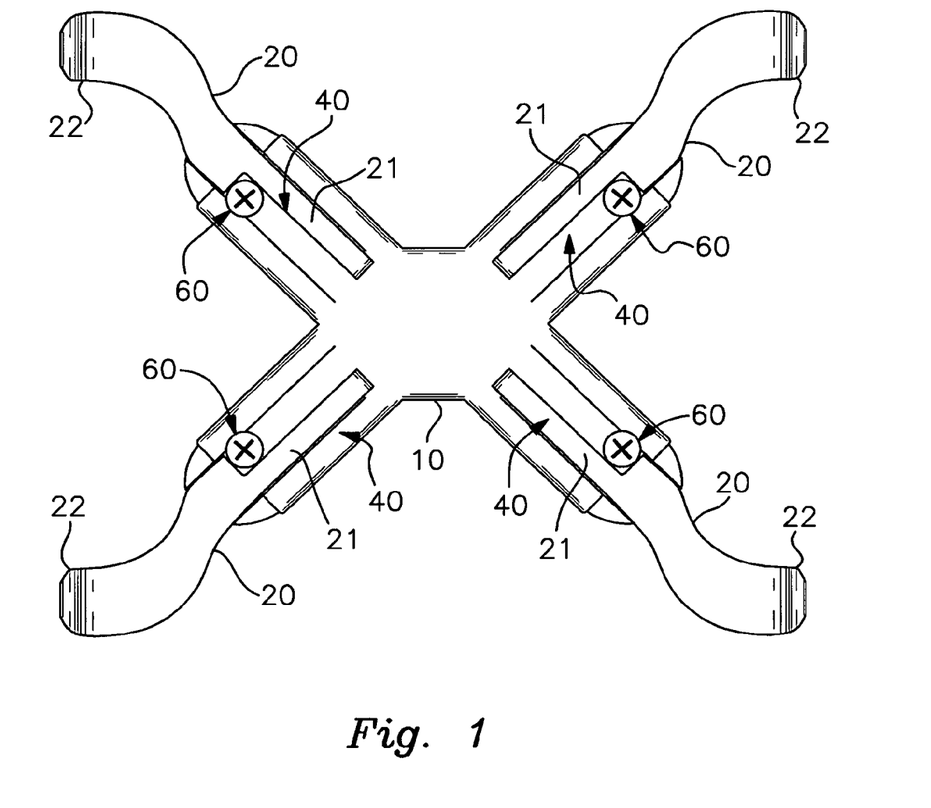
FIG. 1 is a top view of one embodiment of the sternal closure clamp device.

A first embodiment of the invention is illustrated in FIG. 1. The sternal clamp comprises a generally X-shaped central body member 10 that receives and retains four movable or adjustable engagement members 20, the engagement members 20 also defining a general X-shape in configuration and functionality, with each engagement member 20 comprising a generally linear arm member 21 and a projection member 22 joined to the distal end of the arm member 21. The arm members 21 are received by the central body member 10 in a sliding, reciprocating or telescoping manner such that the distance from the projection members 22 to the center of the central body member 10 can be lengthened or shortened. The projection members 22 are hook-like extensions, fingers or the like that extend posteriorly from the arm members 21, preferably generally perpendicularly to the arm members 21. The projection members 22 are each configured and sized so as to fit within the inter-rib space between adjoining ribs, with at least one rib disposed between the pair of projection members 22 on a given side, and with the contact surface of the projection members 22 abutting the outer lateral edges of the sternal halves so as to restrain outward lateral movement by the sternal halves. Two of the engagement members 20 are disposed to one side of the central body member 10 and two of the engagement members 20 are disposed to the other side of the central body member 10. In this manner each sternal half is restrained by two engagement members 20, the separation distance between the projection members 22 of the engagement members 20 on a given side of the central body member 10 being at least greater than the width of a rib so that the engagement members 20 can be positioned to either side of at least one rib. The sternal halves contacting surfaces of the projection members 22 are preferably oriented so as to be generally parallel to each other and generally parallel to the longitudinal sternal incision when the device is in use, such that the contacting surfaces abut the outer edges of the sternal halves in a generally flush manner in order to better distribute the stress applied to the sternal halves.

The engagement members 20 are oriented so as to be non-perpendicular to the sternal incision when the device is in use, with the engagement members 20 on a given side being non-parallel to each other. In other words, the contraction direction for each of the engagement members 20 is non-perpendicular to the sternal incision and non-parallel for engagement members 20 on a given side of the sternal incision. While the angles may vary, it is preferred as shown in FIG. 1 that the angle for each engagement member 20 be at 45 degrees to the sternal incision, such that the two engagement members 20 on a given side are at an angle of 90 degrees to each other.

The engagement members 20 are received by the central body member 10 such that relative movement is possible between the engagement members 20 and the central body member 10, allowing the engagement members 20 to be retracted or contracted so as to shorten the overall width of the device, i.e., such that the distance between projection members 22 on opposing sides of the central body member 10 can be shortened. Preferably, the distance between projection members 22 on opposing sides of the central body member 10 can also be lengthened, the engagement members 20 being extended from the central body member 10, in order to make application of the device to a particular patient easier for the surgeon. In the device of FIG. 1, the engagement arm length adjusting means 40 may comprise a ratchet mechanism, with the arm members 21 of the engagement members 20 being received in a sliding or telescoping manner by the central body member 10, such mechanisms being well known in the art. Engagement member locking means 60, such as for example a threaded mechanical fastener disposed in a threaded aperture, are provided to secure the relative position of the engagement arms 20 when the sternal halves have been brought together, thereby fixing the sternal halves in the abutted position.

In use, the central body member 10 is positioned between the sternal halves across the longitudinal sternal incision with the projection members 22 located in the inter-rib spaces, such that at least one rib is between the two projection members 22 on a given side of the central body member 10. The sternal halves are forced or drawn together to close the longitudinal incision and each of the engagement members 20 is pressed into the central body member 10 such that the sternal halves are retained in abutted relation by the projection members 22 and precluded from separating. Contraction or shortening of the engagement members 21 results in a shorter lateral separation distance between the projection members 22 disposed on opposing sides of the sternum, as well as a shorter separation distance between the pairs of projection members 22 on the same side of the sternum. This latter movement increases the retention force for the sternal halves.

Figure 2:
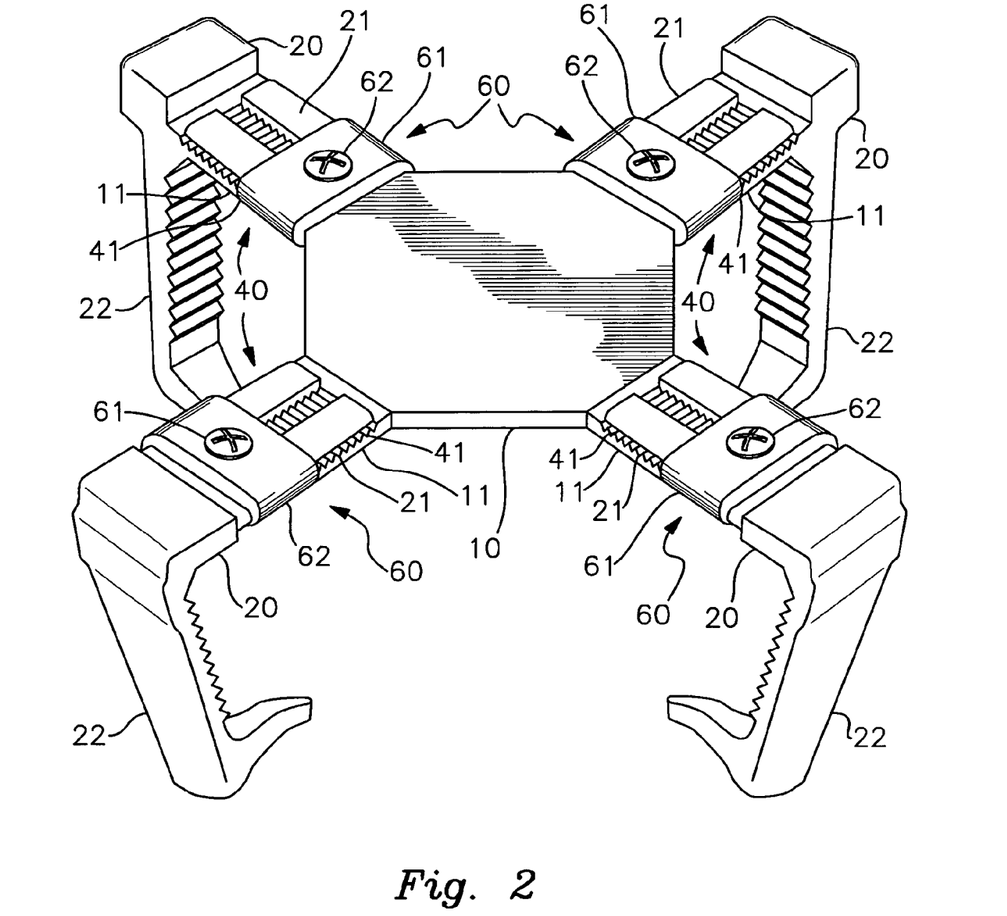
FIG. 2 is a perspective view of an alternate embodiment of the sternal closure clamp device, illustrating a ratchet and set screw combination for the locking means.

In the alternative embodiment shown in FIG. 2, the central body member 10 is again a generally X-shaped body. The projection members 22 of the engagement members 20 further comprise posterior retainer members 23 that extend back toward the middle of the device and are configured to be located behind or posteriorly to the sternal halves when the device is in use. The engagement arm adjustment means 40 in this embodiment comprise interlocking ridges, grooves, ratchets or similar mechanical fixation constructs 41 disposed on the engagement member arm members 21 in combination with interlocking ridges, grooves, ratchets or similar mechanical fixation constructs 11 on the central body member 10, that preclude relative movement between the arm members 21 and the central body member 10 in the extension direction or in both directions when secured by the engagement member locking means 60, which as shown herein comprises a flange member 61 containing a set screw 62 that can be tightened to prevent movement of the engagement members 20.

Figure 3:
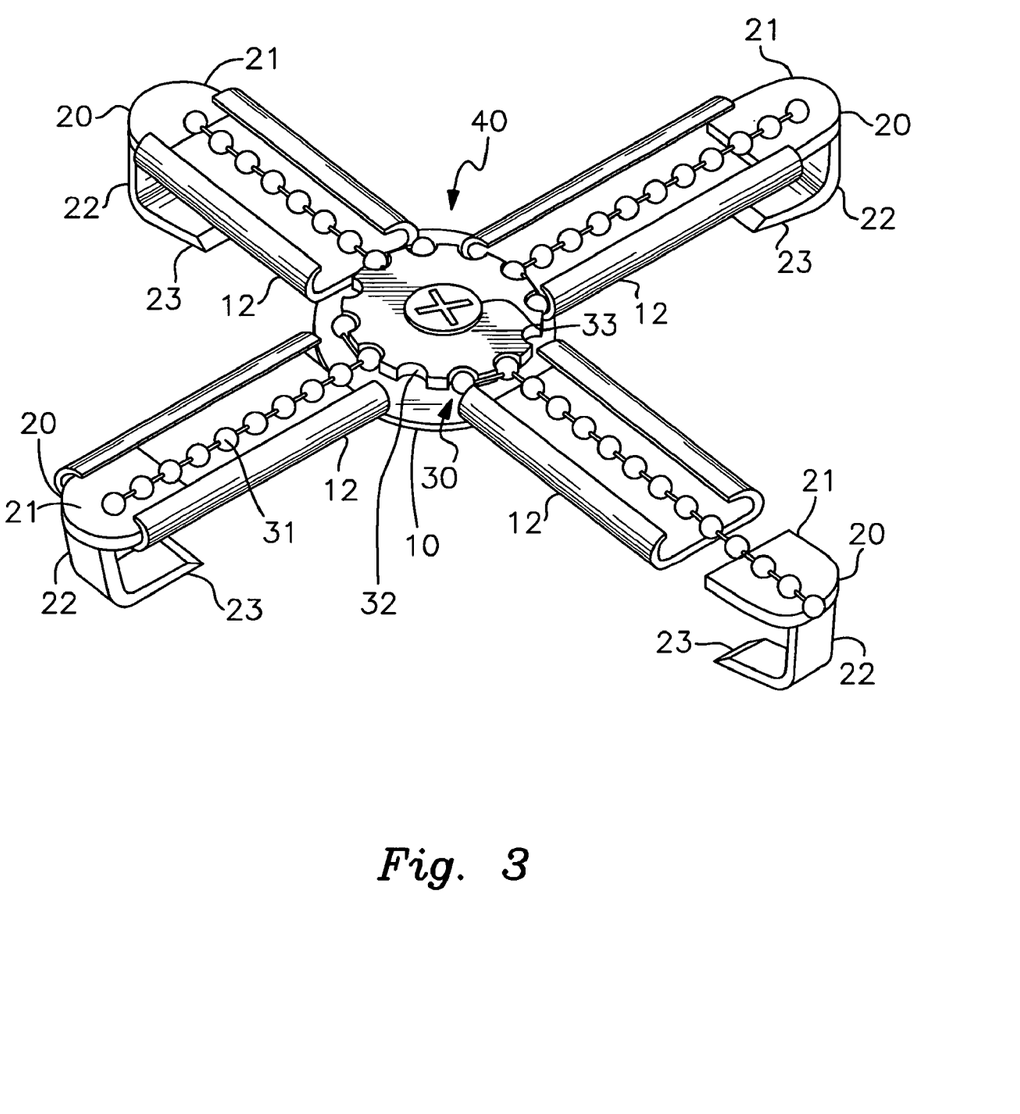
FIG. 3 is a perspective view of an alternate embodiment of the sternal closure clamp device, illustrating a central contracting means.

In the alternative embodiment shown in FIG. 3, the central body member 10 is even more pronouncedly X-shaped and comprises sleeve or channel members 12 that receive the arm members 21 of the engagement members 20 in a sliding or telescoping manner. The engagement arm length adjusting means 40 here includes a centrally located contracting means 30 comprising a rotating gear or knob 32 that retrieves or plays out four chain members 31 depending upon the direction the gear 32 is rotated. The chain members 31 are secured or connected to the engagement members 20 such that distance between opposing engagement members 20 can be shortened or lengthened as required. A tool-receiving member 33, such as a pair of perpendicular slots to receive the end of a screw driver, is provided on the rotational axis of the gear 32 for ease of operation, but flanges or similar handle members could also be substituted. Rotation of the gear 32 results in simultaneous contracting movement of all four engagement members 20.

Figure 4:
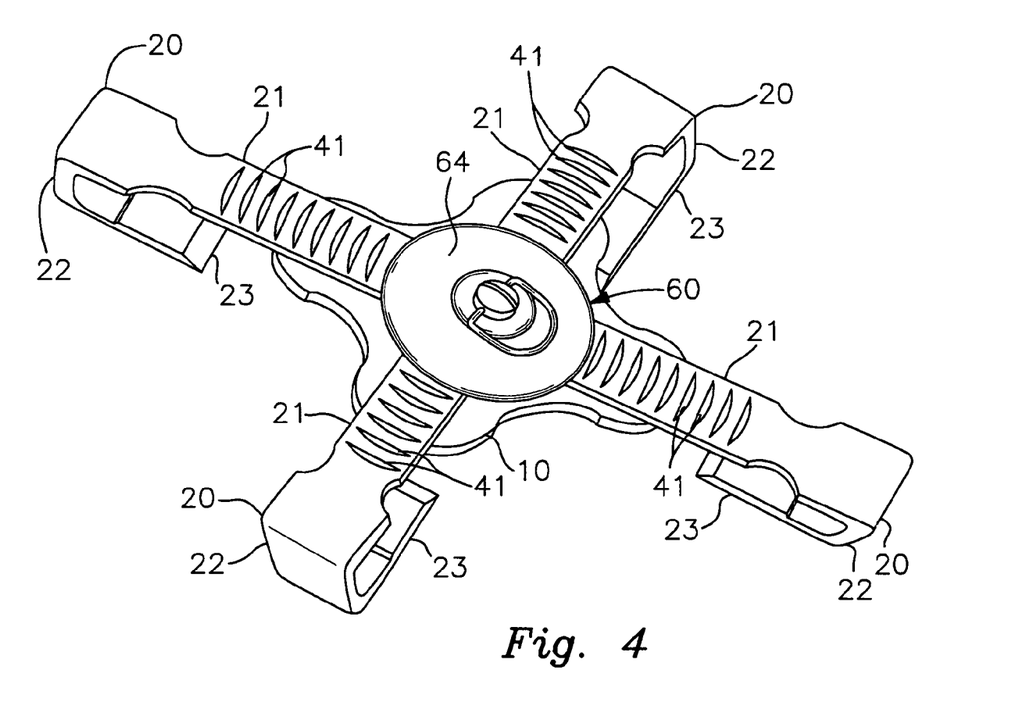
FIG. 4 is a perspective view of an alternate embodiment of the sternal closure clamp device, illustrating a central locking means.
Figure 5:
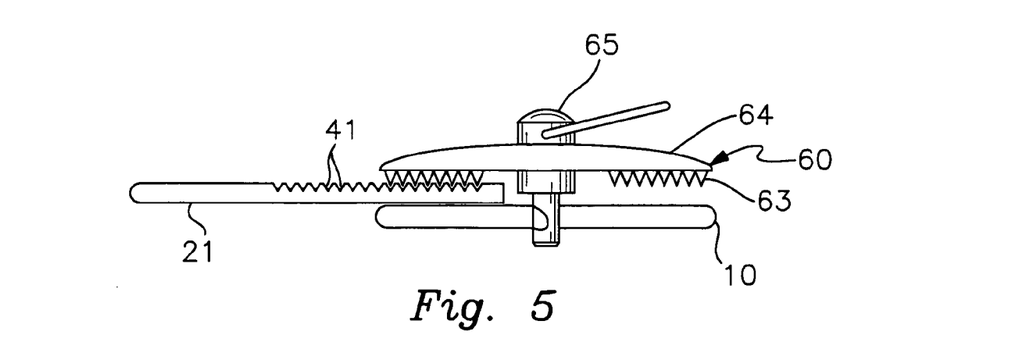
FIG. 5 is a side view illustrating the central locking means of FIG. 4.

Another alternative embodiment for the sternal closure clamp device is shown in FIGS. 4 and 5. In this embodiment, the engagement arm members 21 are provided with grooves, ridges or similar mechanical fixation constructs 41 that cooperate and mate with teeth, grooves or similar mechanical fixation constructs 63 on a releasable cap member 64 that forms the locking means 60 and which is axially mounted on the central body member 10 in a manner that allows the cap member 64 to be raised or separated from the central body member 10 such that the mechanical fixation constructs 41 and 63 are not engaged, thereby allowing relative movement between the engagement members 20 and the central body member 10. The grooves 41 and teeth 63 may be configured to act in a ratchet-like manner, whereby the engagement arms 20 can be forced toward the center of the central body member 10 without manually operating the release member 65 of the cap member 64, with movement of the engagement members 20 in the lengthening direction being precluded or possible only if the cap member 64 is disengaged.

Figures 6, 7, 8:
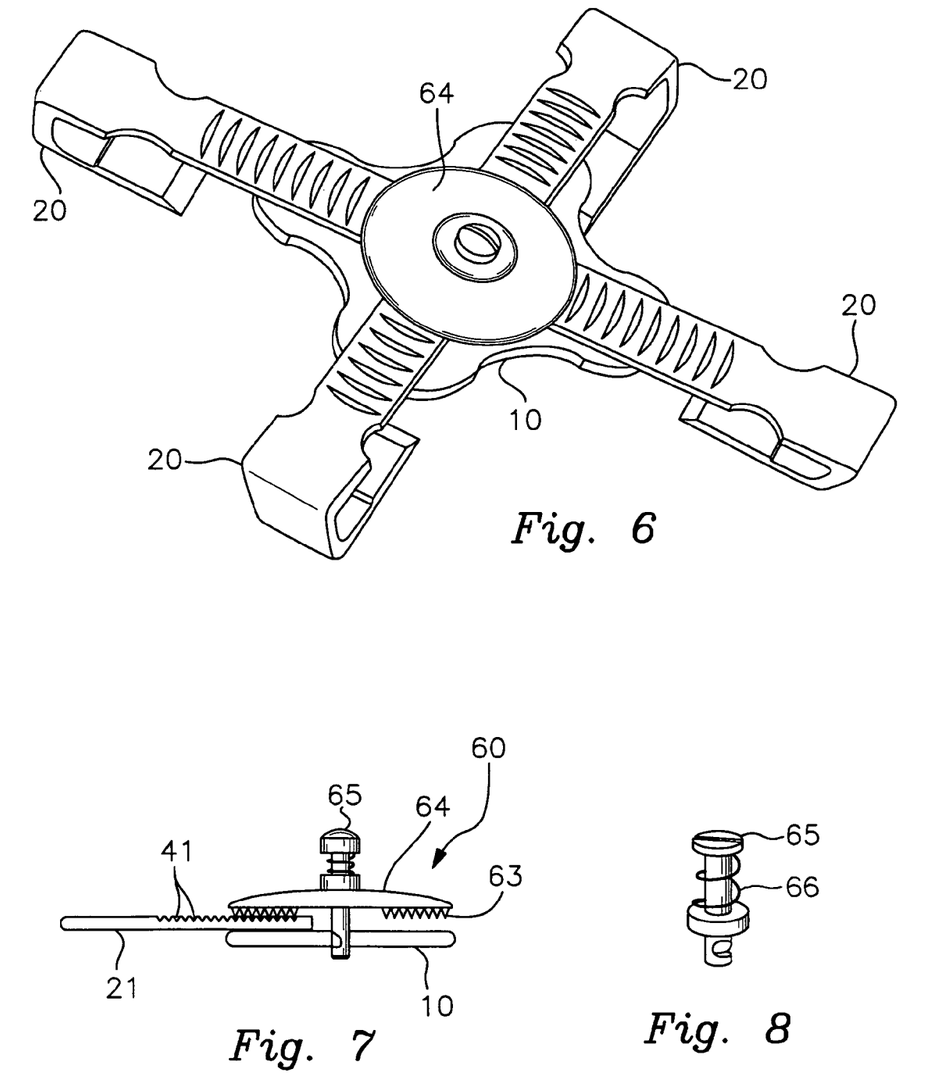
FIG. 6 is a perspective view of an alternate embodiment of the sternal closure clamp device, illustrating an alternative central locking means.
FIG. 7 is a side view illustrating the central locking means of FIG. 6.
FIG. 8 is a side view illustrating the spring release member of the central locking means of FIGS. 6 and 7.

In the alternative embodiment shown in FIGS. 6 through 8, the device is similar to the device illustrated in FIGS. 4 and 5, but here the release member 65 is biased by spring 66 so as to operate automatically to secure the engagement members 20 in the desired position.

Figure 9:
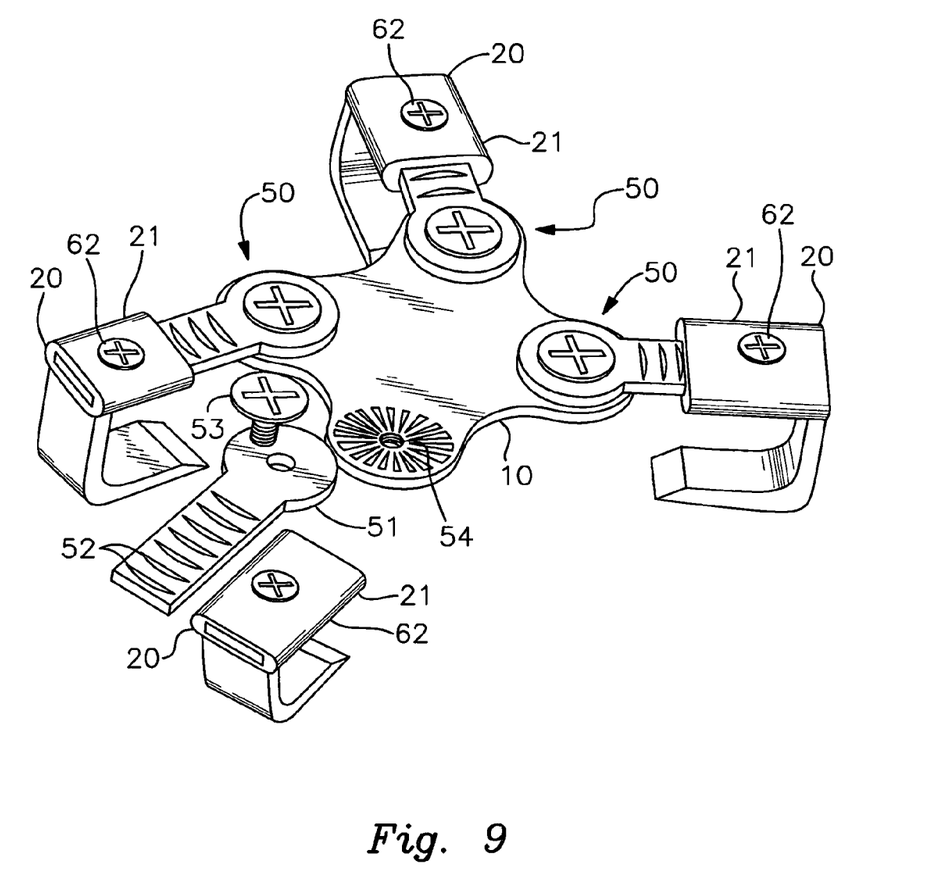
FIG. 9 is a partially expanded perspective view of an alternate embodiment of the sternal closure clamp device, illustrating pivotable engagement members.
Figure 10:
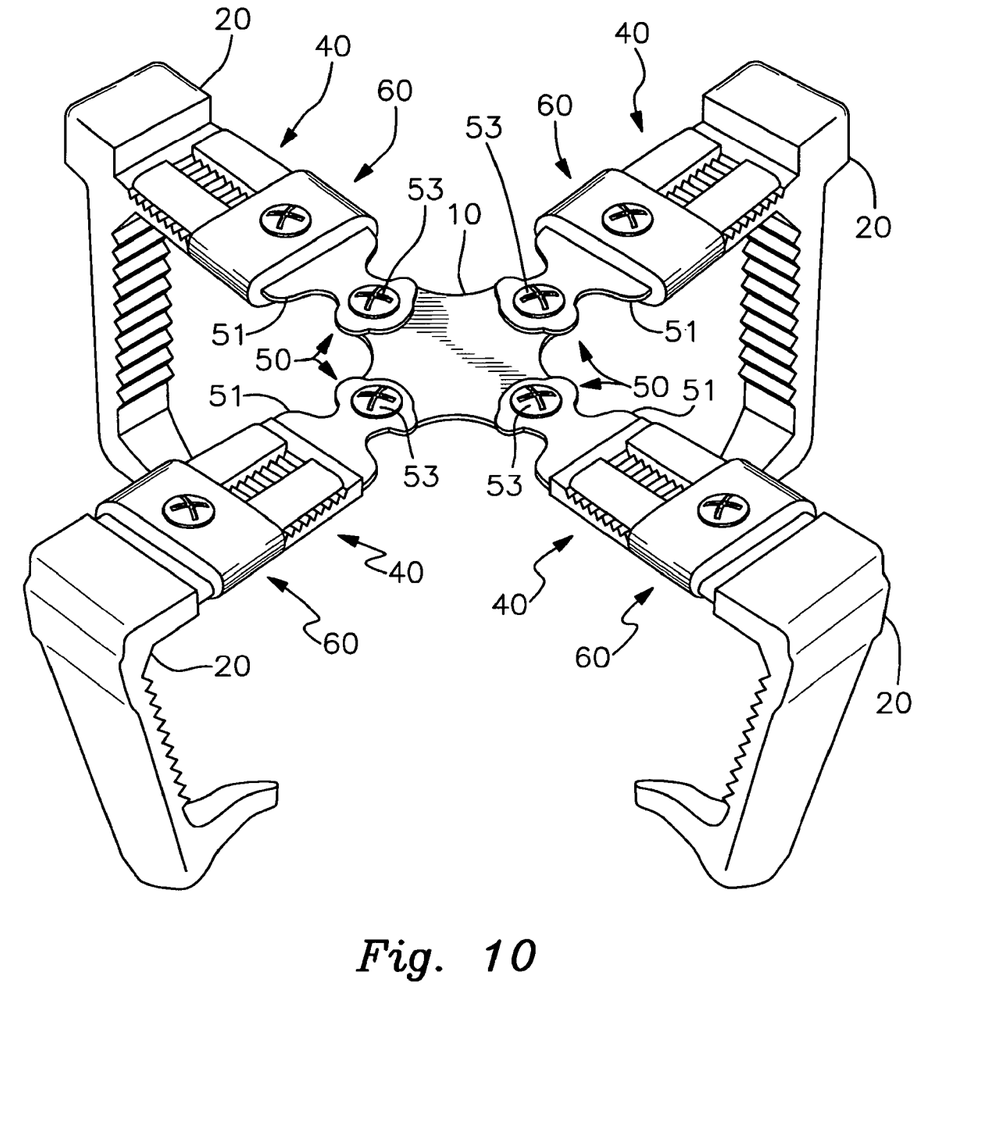
FIG. 10 is a perspective view of an alternate embodiment of the sternal closure clamp device, illustrating alternative pivotable engagement members.

FIGS. 9 and 10 show two alternative embodiments for the sternal closure clamping device that differ from the previous embodiments in that the relative angles of the engagement members 20 to the central body member 10 and to each other are not fixed. Instead, engagement member pivoting means 50 are provided. In the embodiment of FIG. 9, the central body member 10 is provided with four bores 54 that receive pins 53 that secure pivot arms 51 to the central body 10 in a manner that allows the angles of the engagement members 20 to be adjusted relative to the central body member 10 and to each other. The length adjusting means 40 comprise the combination of grooves, ridges, teeth or similar mechanical fixation constructs 52 disposed on the pivot arms 51 and similar grooves, ridges, teeth or similar mechanical fixation constructs disposed within tubular engagement arm members 21. Locking means 60 comprise set screws 62 disposed in the engagement arm members 21.

In the embodiment of FIG. 10, the pivot arms 51 are likewise pivotally connected to the central body member 10 by pins 53, and in this embodiment the engagement member length adjusting means 40 and the engagement member locking means 60 are as described above in reference to FIG. 2. In the embodiments of FIGS. 9 and 10, a more precise abutment and fit between the projection members 22 and the outer lateral edges of the sternal halves can be obtained, since the angles of the engagement members 20 can be adjusted to better conform to the size and natural configuration of the sternum, ribs and inter-rib space.

It is understood that equivalents and substitutions for certain elements described above may be obvious to those skilled in the art, and therefore the true scope and definition of the invention is to be as set forth in the following claims.

We claim:

1. A sternal closure clamp device comprising:
   a central body;
   four independently actuated engagement members, each comprising a telescoping arm member having a longitudinal axis and a projection member, two of said engagement members mounted on a first side of said central body and the other two of said engagement members mounted on a second side of said central body, wherein said arm members of said first side engagement members are positioned such that said first side arm member longitudinal axes are non-parallel to each other and wherein said arm members of said second side engagement member are positioned such that said second side arm member longitudinal axes are non-parallel to each other;
   wherein each of said engagement members are independently retractable toward said central body and independently extendable away from said central body; and
   engagement member locking means for securing said engagement members in a fixed retracted position relative to said central body, said engagement member locking means being releasable such that said engagement members are extendable from said retracted position.

2. The device of claim 1, wherein said first side arm member longitudinal axes are disposed at a ninety degree angle to each other and said second side arm member longitudinal axes are disposed at a ninety degree angle to each other.

3. The device of claim 1, wherein said engagement members are slidingly received by said central body.

4. The device of claim 1, further comprising engagement member pivoting means wherein the angle of each of said engagement members is independently adjustable relative to said central body.

5. The device of claim 1, further comprising engagement member contracting means wherein said engagement members are drawn toward said central body by operation of said contracting means.

6. The device of claim 1, further comprising engagement member length adjusting means, said length adjusting means comprising mechanical fixation constructs disposed on said central body and said engagement members.

7. The device of claim 4, further comprising engagement member length adjusting means, said length adjusting means comprising mechanical fixation constructs disposed on said central body and said engagement members.

8. The device of claim 1, said device being generally X-shaped.

9. The device of claim 1, wherein upon retraction of said engagement members toward said central body the separation distance between said projection members on said first side of said central body is reduced and the separation distance between said projection members on said second side of said central body is reduced.

10. A sternal closure clamp device configured to secure a sternum longitudinally divided into first and second sternal halves in abutting relationship, said device comprising:
 a central body;
 four independently actuated engagement members slidingly received by said central body in a manner whereby each of said engagement members can be retracted toward said central body, each said engagement member comprising a telescoping arm member having a longitudinal axis and a projection member extending generally perpendicularly from each said arm member, two of said engagement members mounted on a first side of said central body and the other two of said engagement members mounted on a second side of said central body, wherein said arm members of said first side engagement members are positioned such that said first side arm member longitudinal axes are non-parallel to each other and with said first side projection members configured to be disposed on opposite sides of a rib of said first sternal half, and wherein said arm members of said second side engagement members are positioned such that said second side arm member longitudinal axes are non-parallel to each other and with said second side projection members configured to be disposed on opposite sides of a rib of said second sternal half;
 wherein each of said engagement members are independently retractable toward said central body and independently extendable away from said central body; and
 engagement member locking means for securing said engagement members in a fixed retracted position relative to said central body, said engagement member locking means being releasable such that said engagement members are extendable from said retracted position.

11. The device of claim 10, wherein said first side arm member longitudinal axes are disposed at a ninety degree angle to each other and said second side arm member longitudinal axes are disposed at a ninety degree angle to each other.

12. The device of claim 10, further comprising engagement member pivoting means wherein the angle of each of said engagement members is independently adjustable relative to said central body.

13. The device of claim 10, further comprising engagement member contracting means wherein said engagement members are drawn toward said central body by operation of said contracting means.

14. The device of claim 10, further comprising engagement member length adjusting means, said length adjusting means comprising mechanical fixation constructs disposed on said central body and said engagement members.

15. The device of claim 12, further comprising engagement member length adjusting means, said length adjusting means comprising mechanical fixation constructs disposed on said central body and said engagement members.

16. The device of claim 10, wherein upon retraction of said engagement members toward said central body the separation distance between said projection members on said first side of said central body is reduced and the separation distance between said projection members on said second side of said central body is reduced.

* * * * *